(12) United States Patent
Sugiyama et al.

(10) Patent No.: US 6,924,131 B2
(45) Date of Patent: Aug. 2, 2005

(54) XYLITOL DEHYDROGENASE OF ACETIC ACID BACTERIA AND GENE THEREOF

(75) Inventors: Masakazu Sugiyama, Kawasaki (JP);
Naoto Tonouchi, Kawasaki (JP);
Shunichi Suzuki, Kawasaki (JP);
Kenzo Yokozeki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 173 days.

(21) Appl. No.: 10/307,385

(22) Filed: Dec. 2, 2002

(65) Prior Publication Data

US 2003/0077797 A1 Apr. 24, 2003

Related U.S. Application Data

(60) Continuation of application No. 09/802,853, filed on Mar. 12, 2001, now abandoned, which is a division of application No. 09/363,189, filed on Jul. 29, 1999, now Pat. No. 6,242,228.

(30) Foreign Application Priority Data

Jul. 30, 1998 (JP) .......................................... 10-216047

(51) Int. Cl.⁷ ............................ C12P 7/18; C12N 15/00; C12N 1/20; C12Q 1/68; C07H 21/04
(52) U.S. Cl. ................. 435/158; 435/320.1; 435/252.3; 435/6; 536/23.2
(58) Field of Search ............................. 435/158, 320.1, 435/252.3, 6; 536/23.2

(56) References Cited

U.S. PATENT DOCUMENTS 3,619,369 A    11/1971   Onishi et al. ................ 435/158
6,303,353 B1   10/2001   Sugiyama et al. ........... 435/158
6,340,582 B1    1/2002   Suzuki et al. ................ 435/158

FOREIGN PATENT DOCUMENTS

WO    WO 94/10325    5/1994
WO    WO 99/20782    4/1999

OTHER PUBLICATIONS

Yoshida et al., Microbiology, 142, 3113–3123, 1996.*
Derwent Publications, AN 1972–27535, JP 47 013707, Apr. 25, 1972, Abstract.
B. Persson, et al., FEBS Letters, Dual Relationships of Xylitol and Alcohol Dehydrogenases in Families of Two Protein Types, Jun. 1993, vol. 324, No. 1, pp. 9–14.
M. A. Gallo, et al., EMBL Database Entry Mmxylitol, Accession No. L34345, 5 pages, "Molecular Characterization of Xylitol Catabolic Pathways in the Enterobacteriaceae", Aug. 4, 1994.

* cited by examiner

*Primary Examiner*—Maryam Monshipouri
(74) *Attorney, Agent, or Firm*—Oblon, Spivak, McClelland, Maier & Neustadt, P.C.

(57) ABSTRACT

Xylitol is produced by allowing xylitol dehydrogenase or cells instoduced with a DNA coding for xylitol dehydrogenase, which is a protein of the following (A) or (B) to act on D-xylulose, and collecting produced xylitol:

(A) a protein which has the amino acid sequence of SEQ ID NO: 4;
(B) a protein which has the amino acid sequence of SEQ ID NO: 4 including substitution, deletion, insertion, addition, or inversion of one or several amino acids, and has xylitol dehydrogenase activity.

12 Claims, 2 Drawing Sheets

US 6,924,131 B2

XYLITOL DEHYDROGENASE OF ACETIC ACID BACTERIA AND GENE THEREOF

CONTINUING APPLICATION INFORMATION

The present application is a continuation of application Ser. No. 09/802,853, filed on Mar. 12, 2001, abandoned, which is a divisional of application Ser. No. 09/363,189, filed on Jul. 29, 1999, now U.S. Pat. No. 6,242,228.

TECHNICAL FIELD

The present invention relates to a novel xylitol dehydrogenase of acetic acid bacteria, gene coding for the same, method for producing xylitol dehydrogenase, and method for producing xylitol. Xylitol is useful in the fields of food industry, drug industry and the like.

BACKGROUND ART

Xylitol, which is a naturally occurring sugar alcohol, is a promising low-calorie sweetener because it has lower calories but exhibits comparable sweetness compared with sucrose. In addition, because of its anti-dental caries property, it can be a dental caries preventive sweetener. Furthermore, because xylitol does not elevate glucose level, it has been utilized for fluid therapy in the treatment of diabetes mellitus. For these reasons, it is expected that the demand of xylitol will increase in future.

The current industrial production of xylitol mainly relies on hydrogenation of D-xylose as disclosed in U.S. Pat. No. 4,008,285. D-Xylose used as a raw material is obtained by hydrolysis of plant materials such as trees, straws, corn cobs, oat hulls and other xylan-rich materials.

However, such D-xylose produced from hydrolysis of plant materials suffers from a drawback that it is rather expensive, and it is arisen from high production cost. For example, the low yield of the hydrolysis treatment of plant materials leads to low purity of the produced D-xylitol. Therefore, the acid used for the hydrolysis and the dyes must be removed by ion exchange treatment after the hydrolysis treatment, and the resulting D-xylose must be further crystallized to remove other hemicellulose saccharides. In order to obtain D-xylose suitable for foodstuffs, further purification would be required. Such ion exchange treatment and crystallization treatment invite the increase of production cost.

Therefore, several methods for producing xylitol have been developed, which utilize readily available raw materials and generate little waste. For example, there have been developed methods for producing xylitol utilizing other pentitols as a starting material. One of such readily available pentitols is D-arabitol, and D-arabitol can be produced by using yeast (*Can. J. Microbiol.*, 31, 1985, 467–471; and *J. Gen. Microbiol.*, 139, 1993, 1047–54).

Thus, several methods for producing xylitol that utilize D-arabitol as a raw material have been developed. One method has been reported in *Applied Microbiology*, 18, 1969, 1031–1035, wherein D-arabitol is produced from glucose by fermentation using *Debaryomyces hansenii* ATCC20121, then converted into D-xylulose using *Acetobacter suboxydans*, and the D-xylulose is converted into xylitol by the action of *Candida guilliermondii* var. soya.

EP 403 392A and EP421 882A disclose methods which comprise producing D-arabitol by fermentation using an osmosis-resistant yeast, then converting D-arabitol into D-xylulose using a bacterium belonging to the genus *Acetobacter, Gluconobacter,* or *Klebsiellal*, forming a mixture of xylose and D-xylulose from the D-xylulose by the action of glucose (xylose) isomerase, and converting the produced mixture of xylose and D-xylulose into xylitol by hydrogenation. There is also disclosed the production of xylitol comprising preliminarily concentrating xylose in the mixture of xylose and D-xylulose and converting the concentrated xylose into xylitol by hydrogenation.

While those methods for the production of xylitol utilizing D-arabitol as a starting material mentioned above can produce xylitol with a relatively high yield, however, they suffer from a drawback that they requires multiple reaction steps, and hence the processes should become complicated. Therefore, they have not been economically acceptable.

On the other hand, breeding of xylitol fermenting microorganisms has been attempted by using genetic manipulation techniques. International Publication WO94/10325 discloses production of xylitol from glucose through fermentation by using a recombinant microorganism obtained by introducing an arabitol dehydrogenase gene derived from a bacterium belonging to the genus *Klebsiella* and a xylitol dehydrogenase gene derived from a bacterium belonging to the genus *Pichia* into an arabitol fermenting microorganism (yeast belonging to the genus *Candida, Torulopsis,* or *Zygosaccharomyces*.

However, such breeding of xylitol fermenting microorganisms by using genetic manipulation techniques as mentioned above is not considered to be completed as a practical means.

By the way, xylitol dehydrogenase is an enzyme that catalyzes the reaction producing xylitol from xylulose, and its presence has been known in various organisms. For example, there has been known the presence of xylitol dehydrogenase in yeast species such as *Pichia stipitis* (*J. Ferment. Bioeng.*, 67, 25 (1989)), *Pachysolen tannophilus* (*J. Ferment. Technol.*, 64, 219 (1986)), *Candida shehatae* (*Appl. Biochem. Biotech.*, 26, 197 (1990)), *Candida parapsilosis* (*Biotechnol. Bioeng.*, 58, 440 (1998)), *Debaryomyces hansenii* (*Appl. Biochem. Biotech.*, 56, 79 (1996)), and *Pullularia pullulans* (*An. Acad. Brasil. Cienc.*, 53, 183 (1981)), filamentous bacteria such as *Aspergillus niger* (*Microbiology*, 140, 1679 (1994)) and *Neurospora crassa* (*FEMS Microbiol. Lett.*, 146, 79 (1997)), algae such as *Galdieria sulphuraria* (*Planta*, 202, 487 (1997)), bacteria such as *Morgannela morganii* (*J. Bacteriol.*, 162, 845 (1985)), and the like.

As for the xylitol dehydrogenase gene, there have been reported nucleotide sequences of the gene derived from *Pichia stipitis* (*FEBS Lett.*, 324, 9 (1993)) and *Morgannela morganii* (DDBJ/GenBank/EMBL accession No. L34345).

However, xylitol dehydrogenase derived from acetic acid bacteria and its gene have not been known so far even for their presence itself.

SUMMARY OF THE INVENTION

The object of the present invention is to provide an enzyme involved in the xylitol biosynthesis of microorganisms excellent in xylitol production ability, genes thereof, and use thereof in order to establish a technique for efficiently producing xylitol or breeding of xylitol fermenting bacteria.

To achieve the aforementioned object, the present inventors searched microorganisms having ability to directly convert D-arabitol to xylitol. As a result, they found that certain bacteria belonging to the genus *Gluconobacter* or *Acetobacter* have such ability. Further, they succeeded in purifying two kinds of xylitol dehydrogenase from one of such bacteria, *Gluconobacter oxydans*, and also succeeded in isolating genes coding for these enzymes and determining their structures. Thus, the present invention has been accomplished.

That is, the present invention provides:
(1) a protein defined in the following (A) or (B):
(A) a protein which has the amino acid sequence of SEQ ID NO: 4 in Sequence Listing;
(B) a protein which has the amino acid sequence of SEQ ID NO: 4 in Sequence Listing including substitution, deletion, insertion, addition, or inversion of one or several amino acids, and has xylitol dehydrogenase activity; and
(2) a protein defined in the following (C) or (D):
(C) a protein which has the amino acid sequence of SEQ ID NO: 6 in Sequence Listing;
(D) a protein which has the amino acid sequence of SEQ ID NO: 6 in Sequence Listing including substitution, deletion, insertion, addition, or inversion of one or several amino acids, and has xylitol dehydrogenase activity.

The present invention also provides:
(3) a DNA which codes for a protein defined in the following (A) or (B):
(A) a protein which has the amino acid sequence of SEQ ID NO: 4 in Sequence Listing;
(B) a protein which has the amino acid sequence of SEQ ID NO: 4 in Sequence Listing including substitution, deletion, insertion, addition, or inversion of one or several amino acids, and has xylitol dehydrogenase activity;
(4) a DNA which codes for a protein defined in the following (C) or (D):
(C) a protein which has the amino acid sequence of SEQ ID NO: 6 in Sequence Listing;
(D) a protein which has the amino acid sequence of SEQ ID NO: 6 in Sequence Listing including substitution, deletion, insertion, addition, or inversion of one or several amino acids, and has xylitol dehydrogenase activity;
(5) the DNA of the above item (3), which is a DNA defined in the following (a) or (b):
(a) a DNA which contains at least a nucleotide sequence corresponding to nucleotide numbers 25 to 1053 of the nucleotide sequence of SEQ ID NO: 3 in Sequence Listing;
(b) a DNA which is hybridizable with a DNA having a nucleotide sequence corresponding to nucleotide numbers 25 to 1053 of the nucleotide sequence of SEQ ID NO: 3 in the Sequence Listing or a probe prepared from the nucleotide sequence under a stringent condition, and codes for a protein having xylitol dehydrogenase activity;
(6) The DNA of above item (5), the stringent condition is a condition in which washing is performed at 60° C., and at a salt concentration corresponding to 1×SSC and 0.1% SDS.
(7) the DNA of the above item (4), which is a DNA defined in the following (c) or (d):
(c) a DNA which contains at least a nucleotide sequence corresponding to nucleotide numbers 1063 to 1848 of the nucleotide sequence of SEQ ID NO: 5 in Sequence Listing;
(d) a DNA which is hybridizable with a DNA having a nucleotide sequence corresponding to nucleotide numbers 1063 to 1848 of the nucleotide sequence of SEQ ID NO: 5 in the Sequence Listing or a probe prepared from the nucleotide sequence under a stringent condition, and codes for a protein having xylitol dehydrogenase activity; and
(8) The DNA of above item (4), the stringent condition is a condition in which washing is performed at 60° C., and at a salt concentration corresponding to 1×SSC and 0.1% SDS.

The present invention also provides:
(9) a cell which is introduced with a DNA of any one of the above items (3) to (8) in such a manner that xylitol dehydrogenase encoded by the DNA can be expressed.

The present invention further provides:
(10) a method for producing xylitol dehydrogenase, which comprises cultivating the cell of the above item (9) in a medium so that xylitol dehydrogenase should be produced and accumulated in the medium, and collecting xylitol dehydrogenase from the medium. The present invention still further provides:
(11) a method for producing xylitol, which comprises allowing xylitol dehydrogenase of the above item (1) or (2) to act on D-xylulose, and collecting produced xylitol; and
(12) a method for producing xylitol, which comprises allowing the cell of the above item (9) to act on D-xylulose, and collecting produced xylitol.

While the xylitol dehydrogenase of the present invention has activity for catalyzing both of the reaction for reducing D-xylulose to produce xylitol, and the reaction for oxidizing xylitol to produce D-xylulose, the expression "having xylitol dehydrogenase activity" herein used means to have at least the activity for catalyzing the reaction producing xylitol from D-xylulose.

According to the present invention, a novel xylitol dehydrogenase and DNA coding for the enzyme are provided, and xylitol dehydrogenase can be produced by using the DNA.

Further, xylitol can be produced by using a cell introduced with the xylitol dehydrogenase or a DNA which codes for the enzyme.

Furthermore, the DNA of the present invention can be utilized for the breeding of xylitol producing microorganisms.

DETAILED DESCRIPTION OF THE INVENTION

Figure 1:
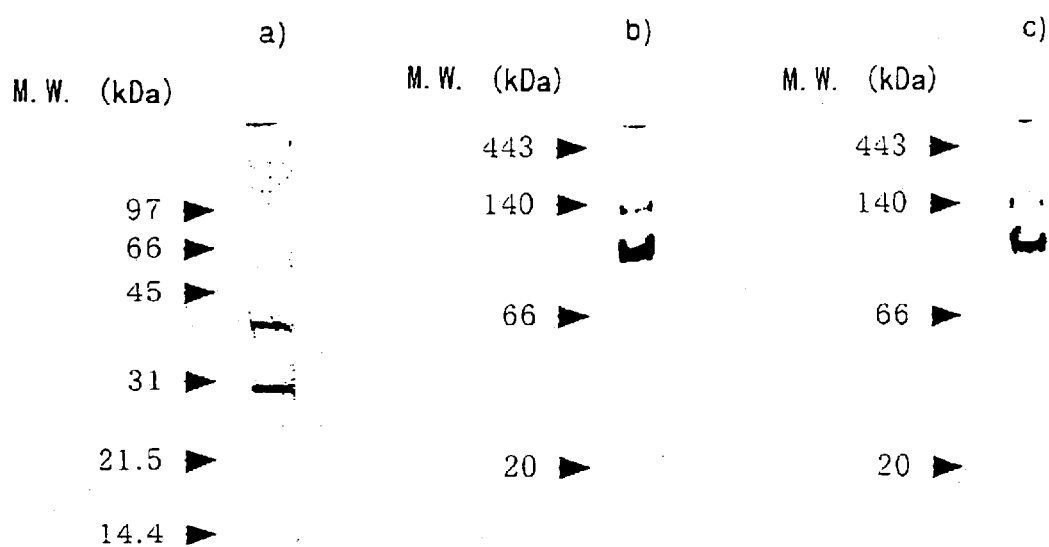
FIG. 1 is a photograph for polyacrylamide gel electrophoresis of purified XDH; a) CBB staining after SDS-PAGE, b) CBB staining after Native-PAGE, and c) activity staining after Native-PAGE.

The present invention will be explained in detail hereafter.
<1> Xylitol Dehydrogenase of the Present Invention The xylitol dehydrogenase of the present invention is an enzyme that is produced by *Gluconobacter oxydans*. Two kinds of such enzyme were found, one was designated as XDH1, and the other as XDH2. XDH1 has the amino acid sequence of SEQ ID NO: 4, and XDH2 has the amino acid sequence of SEQ ID NO: 6 in Sequence Listing. XDH1 and XDH2 show a molecular weight of about 36,000 to about 40,000, and about 27,000 to about 30,000, respectively, as determined by SDS-PAGE (SDS polyacrylamide gel electrophoresis). These two kinds of xylitol dehydrogenase, XDH1 and/or XDH2, may also be collectively referred to as "XDH" hereinafter.

As shown in Example 5 mentioned hereinafter, the optimum pH for XDH2 in the reduction reaction (reaction producing xylitol from D-xylulose) was around 5. The optimum pH for the reduction reaction of well-known xylitol dehydrogenases, for example, xylitol dehydrogenase derived from *Asperhillus niger* is strictly 6.5 (Cor F. B. Witteveen, et al., *Microbiology*, 140, 1679–1685, 1994), and therefore they are clearly different from XDH2 of the present invention derived from *Gluconobacter* bacteria in the optimum reaction pH.

As an example of the method for producing XDH of the present invention, methods utilized for isolation and purification of XDH from *Gluconobacter oxydans* will be explained below.

First, cells of *Gluconobacter oxydans*, for example, the strain ATCC621, are disrupted by a mechanical means such as ultrasonication, or an enzymatic means utilizing a cell wall digesting enzyme etc., and a cell extract is prepared by removing the insoluble fraction therefrom by centrifugation or the like.

The cell extract obtained as described above can be fractinated by a combination of conventional purification methods for proteins such as anion exchange chromatography, affinity chromatography, hydrophobic chromatography, and gel filtration chromatography, to purify XDH.

As a carrier for anion exchange chromatography, Q-Sepharose FF (produced by Pharmacia), Mono-Q (produced by Pharmacia) and the like can be mentioned. The extract containing XDH is passed through a column filled with such a carrier so that the enzyme should be adsorbed on the column, and, after washing the column, the enzyme is eluted with a buffer of high salt concentration. In this case, the salt concentration may be raised stepwise, or a concentration gradient may be applied. For example, when Q-Sepharose FF is used, XDH adsorbed on the column may be eluted with 200 to 350 mM KCl. In the case of Mono-Q, it may be eluted with 150 to 250 mM KCl.

As a carrier for affinity chromatography, HiTrap Blue (produced by Pharmacia) can be mentioned. The XDH of the present invention utilizes NAD or NADH as a coenzyme, and hence has affinity for these substances. XDH adsorbed on the carrier can be eluted with a buffer containing about 5 mM NAD.

As a carrier for hydrophobic chromatography, Phenyl Sepharose HP (produced by Pharmacia) can be mentioned. XDH adsorbed on the carrier at a low salt concentration can be eluted with about 200 to 300 mM ammonium sulfate.

The XDH purified as described above can be further purified and separated into XDH1 and XDH2 by gel filtration chromatography, SDS-PAGE or the like. As a carrier for gel filtration chromatography, Sephadex 200HP (produced by Pharmacia) can be mentioned.

In the aforementioned purification procedure, if a fraction contains XDH or not can be confirmed by measuring the XDH activity of the fraction by, for example, the method shown in the examples mentioned hereinafter.

The N-terminus amino acid sequences of XDH1 and XDH2 purified as described above are shown as SEQ ID NO: 1 and SEQ ID NO: 2 in Sequence Listing, respectively.

While the XDH of the present invention can be obtained from cells of *Gluconobacter oxydans* by isolation and purification as described above, it can also be produced by introducing a DNA which codes for XDH mentioned hereinafter into a suitable host so that expression of the DNA should be obtained in accordance with a conventionally used method for producing heterogenous proteins by fermentation.

The various genetic recombination techniques mentioned below are described in Molecular Cloning, 2nd edition, Cold Spring Harbor Press (1989).

As a host for obtaining the expression of the XDH gene, various prokaryotic cells including *Escherichia* bacteria such as *Escherichia coli, Gluconobacter* bacteria such as *Gluconobacter oxydans*, and *Bacillus subtilis*, and various eukaryotic cells including *Saccharomyces cerevisiae, Pichia stipitis* and *Aspergillus oryzae* can be used.

A recombinant DNA used for introducing the XDH gene into a host can be produced by inserting a DNA coding for XDH into a vector selected depending on the kind of the host in which the expression is to be obtained in such a manner that the expression of XDH encoded by the DNA can be possible. When an XDH gene specific promoter can function in the host cell, that promoter can be used as the promoter for the expression of the XDH gene. Further, if required, another promoter that can function in the host cell may be ligated to a DNA coding for XDH to obtain the expression under the control of that promoter. When *Escherichia* bacteria are used as a host, as examples of such a promoter, lac promoter, trp promoter, trc promoter, tac promoter, $P_R$ promoter, $P_L$ promoter of lambda phage and the like can be mentioned. As vectors for *Escherichia* bacteria, pUC19, pUC18, pBR322, pHSG299, pHSG298, pHSG399, pHSG398, RSF1010, pMW119, pMW118, pMW219, pMW218 and the like can be mentioned. Phage DNA vectors can also be utilized. Furthermore, an expression vector containing a promoter and capable of expressing an inserted DNA sequence can also be used.

*E. coli* can be transformed by introducing a plasmid in accordance with, for example, a method of D. A. Morrison (*Methods in Enzymology*, 68, 326 (1979)) or a method in which recipient cells are treated with calcium chloride to increase permeability for DNA (Mandel, M. and Higa, A., *J. Mol. Biol.*, 53, 159 (1970)).

<2> DNA Coding for XDH

A DNA coding for XDH can be obtained from a cDNA library or chromosome DNA library of *Gluconobacter oxydans* by PCR (polymerase chain reaction, see White, T. J. et al; *Trends Genet.*, 5, 185 (1989)) or hybridization. Primers used for PCR can be designed based on the amino acid sequences of the amino termini determined for the purified XDH1 and XDH2. Further, since the nucleotide sequences of XDH1 gene (SEQ ID NO: 3) and XDH2 gene (SEQ ID NO: 5) have been elucidated according to the present invention, primers or probes for hybridization can be designed based on those nucleotide sequences. By using primers having sequence corresponding to 5' non-translation region and 3' non-translation region as primers for PCR, the XDH coding region can be amplified in its full length. Specifically, as for XDH2, a primer having a nucleotide sequence of a region upstream from the nucleotide number 1063 in SEQ ID NO: 5 can be used as the 5' primer, and a primer having a sequence complementary to a nucleotide sequence of a region downstream from the nucleotide number 1851 can be used as the 3' primer. As for XDH1, a primer having a nucleotide sequence of a region upstream from the nucleotide number 25 in SEQ ID NO: 3 can be used as the 5' primer.

Synthesis of the primers can be performed by an ordinary method such as a phosphoamidite method (see *Tetrahedron Letters*, 22, 1859 (1981)) by using a commercially available DNA synthesizer (for example, DNA Synthesizer Model 380B produced by Applied Biosystems). Further, the PCR can be performed by using, for example, Gene Amp PCR System 9600 produced by PERKIN ELMER and using TaKaRa LA PCR in vitro Cloning Kit (supplied by Takara Shuzo Co., Ltd.) in accordance with a method designated by the suppliers.

The DNA of the present invention may code for XDH1 or XDH2 including substitution, deletion, insertion, addition, or inversion of one or several amino acids at one or a plurality of positions provided that the activity to produce xylitol from D-xylose of XDH1 or XDH2 encoded thereby is not deteriorated. Although the number of "several" amino acids differs depending on the position or the type of amino acid residues in the three-dimensional structure of the protein, it may be 2 to 100, preferably 2 to 50, and more preferably 2 to 10.

DNA, which codes for the substantially same protein as XDH1 or XDH2 as described above, is obtained, for example, by modifying the nucleotide sequence of XDH1 gene or XDH2 gene, for example, by means of the site-directed mutagenesis method so that one or more amino acid residues at a specified site of the gene involve substitution, deletion, insertion, addition, or inversion. DNA modified as described above may be obtained by the conventionally known mutation treatment. The mutation treatment includes a method for treating DNA coding for XDH in vitro, for example, with hydroxylamine, and a method for treating a microorganism, for example, a bacterium belonging to the genus Escherichia harboring DNA coding for XDH with ultraviolet irradiation or a mutating agent such as N-methyl-N'-nitro-N-nitrosoguanidine (NTG) and nitrous acid usually used for the mutation treatment.

The substitution, deletion, insertion, addition, or inversion of nucleotide as described above also includes mutation (mutant or variant) which naturally occurs, for example, the difference in strains, species or genera of the microorganism.

The DNA, which codes for substantially the same protein as XDH1 or XDH2, is obtained by expressing DNA having mutation as described above in an appropriate cell, and investigating the XDH1 or XDH2 activity of an expressed product. The DNA, which codes for substantially the same protein as XDH1 or XDH2, is also obtained by isolating DNA which is hybridizable with DNA having, for example, a nucleotide sequence corresponding to nucleotide numbers of 25 to 1053 of the nucleotide sequence of SEQ ID NO: 3 or a probe which can be prepared from the DNA, or a nucleotide sequence corresponding to nucleotide numbers of 1063 to 1848 of the nucleotide sequence of SEQ ID NO: 5 or a probe which can be prepared from the DNA, under a stringent condition, and which codes for a protein having the XDH1 or XDH2 activity, from DNA coding for XDH1 or XDH2 having mutation or from a cell harboring it. The "stringent condition" referred to herein is a condition under which so-called specific hybrid is formed, and non-specific hybrid is not formed. It is difficult to clearly express this condition by using any numerical value. However, for example, the stringent condition includes a condition under which DNA's having high homology, for example, DNA's having homology of not less than 50% are hybridized with each other, and DNA's having homology lower than the above are not hybridized with each other. Alternatively, the stringent condition is exemplified by a condition under which DNA's are hybridized with each other at a salt concentration corresponding to an ordinary condition of washing in Southern hybridization, i.e., 60° C., 1×SSC, 0.1% SDS, preferably 0.1×SSC, 0.1% SDS.

The gene, which is hybridizable under the condition as described above, includes those having a stop codon generated in the gene, and those having no activity due to mutation of active center. However, such mutant genes can be easily removed by ligating the gene with a commercially available activity expression vector, and measuring the XDH1 or XDH2 activity in accordance with the method described below.

A DNA which codes for the XDH of the present invention can be used for, in addition to the method for producing XDH mentioned above and the method for producing xylitol mentioned below, breeding of xylitol producing microorganisms. For example, by enhancing the XDH gene in a microorganism having the ability to convert D-arabitol into xylitol, e.g., Gluconobacter bacteria, the ability of the microorganism to convert D-arabitol into xylitol can be increased.

<3> Method for Producing Xylitol

Xylitol can be produced by allowing the XDH of the present invention or a cell introduced with a DNA which codes for XDH and expresses XDH to act on D-xylulose, and collecting produced xylitol.

XDH may be an enzyme extracted from Gluconobacter bacteria, or an enzyme produced by a genetic recombination technique utilizing a DNA which codes for XDH. Further, XDH may be either XDH1 or XDH2, and may be a mixture of them at an arbitrary ratio.

The reaction producing xylitol from D-xylulose usually provides good results when performed at a temperature of 20–60° C., more preferably 30–40° C., and pH of 4–10, more preferably pH of 4–8. For the reaction, either of standing culture or spinner culture may be used. While the reaction time may vary depending on concentration of XDH, amount of cells, and substrate concentration to be used, it is desirably 1–100 hours.

For collecting and separating the produced xylitol from a finished reaction mixture, any conventional methods including use of a synthetic adsorbent, precipitant, or the like may be used.

BEST MODE FOR CARRYING OUT THE INVENTION

The present invention will be further explained more specifically with reference to the following examples hereinafter. However, the present invention is not limited by the descriptions of the examples.

EXAMPLE 1

Production of XDH by Gluconobacter oxydans and Purification Thereof

<1> Culture of Gluconobacter oxydans ATCC621

The Gluconobacter oxydans strain ATCC621 was cultured to obtain its cells having sufficient XDH activity. The cultivation was always performed in PD medium as broth culture with shaking at 30° C. The PD medium had a composition of 24 g/L potato dextrose (Difco), 30 g/L yeast extract (Difco), 5 g/L meat extract (Difco), 15 g/L glycerol, 10 g/L D-arabitol, 10 g/L D-xylose, 10 g/L xylitol, 20 g/L calcium carbonate (Kanto Chemical), pH 7.0.

First, as a seed culture, the strain ATCC621 was inoculated into a Sakaguchi flask containing 40 ml of PD medium, and cultured overnight with shaking at 30° C. The obtained culture broth was inoculated in an amount corresponding to 1% into 40 Sakaguchi flasks each similarly containing 40 ml of PD medium, and cultured with shaking for 3 days at 30° C. (main culture). After removing calcium carbonate by centrifugation, the cells were collected by centrifugation. The cells obtained as described above were used as a material for purification of XDH.

The XDH activity was determined by the following enzyme activity assay. 30 $\mu$l of enzyme solution was added to 570 $\mu$l of a reaction solution containing 100 mM (final concentration) xylitol, 2 mM NAD, and 100 mM CAPS (pH 10.0) to perform the enzymatic reaction at 30° C., and the increase of NADH produced as the reaction proceeded was determined by measuring the absorbance at 340 nm using a spectrophotometer (DU640 Spectrometer produced by BECKMAN). The activity producing 1 μmol of NADH per minute was defined as 1 unit (U). The calculation was performed by using the molecular absorption coefficient ε of NADH at 340 nm of 6.3×10³.

<2> Purification of XDH (1) Preparation of Cell Extract

The cells obtained above were suspended in 50 mM potassium phosphate buffer (pH 7), and centrifuged at 5000×g for 10 minutes to be collected again in the precipitated fraction. The procedure comprising suspension and centrifugation of these cells was repeated twice to wash the cells.

About 10 g of the washed cells were suspended in 50 ml of Buffer 1 (20 mM Tris-HCl (pH 7.6), 0.5 mM EDTA, 1 mM MgCl₂, 1 mM DTT), and disrupted by sonication for 20 minutes at 4° C. The disrupted cell suspension was centrifuged (8000 rpm, 10 minutes) to remove the cell debris, and further ultracentrifuged (56000 rpm, 30 minutes) to remove the insoluble fraction. Thus, a soluble fraction was obtained.

(2) Anion Exchange Chromatography

The above-obtained soluble fraction was loaded on an anion exchange chromatography column Q-Sepharose FF (produced by Pharmacia) equilibrated with Buffer 1. By this operation, XDH was adsorbed on the carrier.

The protein not adsorbed on the carrier (non-adsorbed proteins) was washed off by using Buffer 1, and then the adsorbed protein was eluted by using a buffer containing KCl as an eluate. In this elution, KCl concentration in the buffer was linearly changed from 0 M to 0.5 M. The XDH activity was measured for each eluted fraction obtained by this elution, and the XDH activity was found in eluted fractions corresponding to the KCl concentration of about 200 to 350 mM.

(3) NAD Affinity Chromatography

The above-obtained fractions containing the XDH activity were combined, and dialyzed against Buffer 1. The solution after the dialysis was filtered through a 0.45 μm filter. The obtained filtrate was loaded on an NAD affinity column HiTrap Blue 5 ml (produced by Pharmacia) equilibrated with Buffer 1. By this operation, XDH was adsorbed on the carrier.

The protein not adsorbed on the carrier (non-adsorbed proteins) was washed off by using Buffer 1, and then the adsorbed protein was eluted by using Buffer 2 (20 mM Tris-HCl (pH7.6), 0.5 mM EDTA, 1 mM MgCl₂, 1 mM DTT, 5 mM NAD) containing NAD as an eluate. As a result, XDH was detected in the eluted fractions.

(4) Anion Exchange Chromatography

The aforementioned eluted fractions containing XDH activity were filtered through a 0.45 μm filter. The obtained filtrate was loaded on an anion exchange chromatography column Mono-Q (produced by Pharmacia) equilibrated with Buffer 1. By this operation, XDH was adsorbed on the carrier.

The protein not adsorbed on the carrier was washed off by using Buffer 1, and then the adsorbed protein was eluted by using a buffer containing KCl as an eluate. This elution was performed by linearly changing KCl concentration in the buffer from 0 mM to 500 mM. The XDH activity was measured for each eluted fraction obtained by this elution, and the XDH activity was found in eluted fractions corresponding to the KCl concentration of about 150 to 250 mM.

(5) Hydrophobic Chromatography

The eluted fractions for which the activity was detected were dialyzed against Buffer 3 (50 mM potassium phosphate buffer, 1 M ammonium sulfate, pH 7.0). The solution obtained after the dialysis was filtered through a 0.45 μm filter. The obtained filtrate was loaded on a hydrophobic chromatography column Phenyl Sepharose HP (produced by Pharmacia) equilibrated with Buffer 3. By this operation, XDH was adsorbed on the carrier.

The protein not adsorbed on the carrier was washed off by using Buffer 3, and then the adsorbed protein was eluted by using Buffer 4 (50 mM potassium phosphate buffer, pH 7.0) as an eluate. For this elution, ammonium sulfate concentration in the buffer was linearly changed from 1 M to 0 M. The XDH activity was measured for each eluted fraction obtained by this elution, and the XDH activity was found in eluted fractions corresponding to the ammonium sulfate concentration of about 200 to 300 mM.

(6) Analysis of Purified Fraction

The XDH-active fraction obtained by the aforementioned purification was subjected to SDS-PAGE and stained with Coomassie Brilliant Blue. As a result, it was confirmed that XDH had been purified to such a level that XDH could be detected as two bands, and their molecular weights were estimated to be about 27,000 to abut 30,000, and about 37,000 to about 40,000, respectively (see FIG. 1). Henceforth, the protein corresponding to the band of molecular weight of about 36,000 to abut 40,000 is referred to as XDH1, and the protein corresponding to the band of molecular weight of about 27,000 to about 30,000 as XDH2.

Further, the obtained active fraction was subjected to Native-PAGE (non-denaturation PAGE), and stained with Coomassie Brilliant Blue. As a result, two bands corresponding to molecular weights of more than 100 kDa were confirmed. When the gel after Native-PAGE was subjected to activity staining with an activity staining solution (25 mM glycine buffer, 2.5 mM NAD, 50 mM xylitol, 0.2 nM phenazine methosulfate, 0.2 mM tetranitro blue tetrazolium chloride), the XDH activity was detected in both of the two corresponding bands, and it was confirmed that both of the proteins corresponding to the two bands detected in the SDS-PAGE had XDH activity (FIG. 1). The purified fraction containing these XDH1 and XDH2 will sometimes be referred to simply as XDH hereinafter.

The increase of the XDH specific activity as a result of the aforementioned purification was determined. The XDH activity of the aforementioned cell extract and the active fraction obtained by the purification was measured. As a result, it was found that the specific activity per unit protein weight was increased by about 550 times by the series of purification procedures. By the activity assay method used for this measurement, the specific activity of the purified XDH was estimated to be about 130 U/mg (30° C., pH 10).

(7) Determination of Amino Acid Sequence at Amino Terminus of XDH

The N-terminus sequence of the XDH purified as described above was sequenced as follows. That is, about 10 μg in terms of protein of the purified XDH fraction was electrophoresed in polyacrylamide gel in the presence of SDS, and then the XDH in the gel was blotted to a membrane filter, and analyzed for the amino acid sequence from the N-terminus by a protein sequencer. Specifically, the objective enzymes were blotted to a polyvinylidene fluoride (PVDF) membrane from the gel after the electrophoresis by the semi-dry method (Tanpakushitu Kozo Kaiseki [Analysis of Protein Structure], H. Hirano, Tokyo Kagaku Dojin) by using Milliblot (Millipore). Then, the objective enzymes (XDH1 and XDH2) on the PVDF film were analyzed by a protein sequencer (Model 476A produced by ABI) to perform N-terminus amino acid sequence analysis.

As a result, the amino acid sequence of 27 residues from the N-terminus was determined for XDH1, and the amino acid sequence of 25 residues from the N-terminus was determined for XDH2. The amino acid sequence of the determined N-terminus sequence of XDH1 was shown as SEQ ID NO: 1 in Sequence Listing, and the amino acid sequence of the N-terminus sequence of XDH2 was shown as SEQ ID NO: 2 in Sequence Listing, respectively.

EXAMPLE 2

Conversion of D-xylulose into Xylitol by XDH

D-Xylulose was converted into xylitol using the purified XDH (XDH1 and XDH2) obtained in Example 1. 0.2 U of the purified XDH was added to 0.25 ml of a reaction solution containing 21 mM D-xylulose, 20 mM NADH, and 100 mM Tris-HCl buffer (pH 8.0), and incubated at 30° C. for 1 hour to allow the reaction. The solution after the reaction was subjected to high performance liquid chromatography (HPLC) to analyze the produced xylitol under the following conditions.

Column: Shodex SC1211 (produced by Showa Denko Co., Ltd.)
Mobile phase: 50% acetonitrile/50% 50 ppm aqueous Ca-EDTA
Flow rate: 0.8 ml/minute
Temperature: 60° C.
Detection: RI detector As a result, formation of 18 mM xylitol was observed in the solution after the reaction, and it was shown that xylitol could be produced from D-xylulose using the purified XDH.

EXAMPLE 3

Isolation of XDH Gene Derived from *Gluconobacter*

<1> Amplification of XDH Gene Fragment by PCR (1) Preparation of PCR Primers Based on N-terminus Amino Acid Sequence of XDH Based on each of the aforementioned N-terminus amino acid sequences (SEQ ID NOS: 1 and 2) of XDH (XDH1, XDH2) derived from *Gluconobacter oxydans* ATCC621, mixed primers which had the nucleotide sequences shown as SEQ ID NO: 7–10, respectively, were prepared.

(2) Preparation of Chromosome DNA of *Gluconobacter oxydans* ATCC621

*Gluconobacter oxydans* ATCC621 strain was cultured under the following conditions. First, the ATCC621 strain was cultured in 20 ml of YPG medium (3% glucose, 0.5% Bacto yeast extract, 0.3% Bacto peptone, pH 6.5) overnight as a seed culture. By using 5 ml of this culture as seed bacteria, main culture was performed using 100 ml of YPG medium. The culture was performed with shaking at 30° C.

After the bacteria were cultured to late log phase under the aforementioned conditions, 100 ml of the culture broth was centrifuged (12000×g, 4° C., 15 minutes) to collect the cells. The cells were suspended in 10 ml of 50:20 TE (50 mM Tris-HCl, pH 8.0, 20 mM EDTA), and the cells were washed and recovered by centrifugation. The cells were suspended in 10 ml of 50:20 TE again. To this suspension, 0.5 ml of 20 mg/ml lysozyme solution and 1 ml of 10% SDS solution were added, and incubated at 55° C. for 20 minutes. After the incubation, deproteinization was performed by adding equal volume of 10:1 TE-saturated phenol. DNA was precipitated by adding equal volume of 2-propanol to the separated aqueous layer, and collected. The precipitated DNA was dissolved in 0.5 ml of 50:20 TE, added with 5 μl of 10 mg/ml RNase and 5 μl of 10 mg/ml Proteinase K, and allowed to react at 55° C. for 2 hours. After the reaction, deproteinization was performed by adding equal volume of 10:1 TE-saturated phenol. The separated aqueous layer was further added with equal volume of 24:1 chloroform/isoamyl alcohol, and stirred, and the aqueous layer was collected. After this procedure was further repeated twice, the obtained aqueous layer was added with 3 M sodium acetate solution (pH 5.2) so that a final concentration of 0.4 M should be obtained, and further added with twice as much volume of ethanol. The produced DNA was collected as precipitates, washed with 70% ethanol, dried, and dissolved in 1 ml of 10:1 TE.

(3) Preparation of DNA Fragment by PCR

The DNA molecule containing the gene coding for XDH derived from *Gluconobacter* bacteria was amplified and isolated by PCR using TaKaRa LA PCR in vitro Cloning Kit (supplied by Takara Shuzo Co., Ltd.). The experiments were performed according to the instruction attached to the kit hereafter unless otherwise indicated.

Five μg of the chromosome DNA produced as described in the above (2) was digested with restriction enzymes PstI or HindIII respectively. Then, a PstI cassette or HindIII cassette was ligated to the DNA fragments collected by the ethanol precipitation. Furthermore, after performing ethanol precipitation, first PCR was performed for the collected DNA by using a combination of primers of the primer C1 and primers mentioned below. That is, a DNA ligated to PstI cassette was used as a template DNA for the primer XDH1-S1 that was based on the amino acid sequence of XDH1, and a DNA ligated to HindIII cassette was used as a template DNA for the primer XDH2-S1 that was based on the sequence of XDH2, respectively. There are shown the nucleotide sequences of the primer C1, the primer XDH1-S1, and the primer XDH2-S1 as SEQ ID NO: 11, SEQ ID NO: 7, and SEQ ID NO: 9 in Sequence Listing, respectively. The primer C1 was contained in the TaKaRa LA PCR in vitro Cloning Kit, and corresponded to the sequence in the PstI cassette and the HindIII cassette. The PCR reaction was performed by using Gene Amp PCR System 9600 (produced by PERKIN ELMER), and a reaction according to the following conditions was repeated for 30 cycles.

94° C. for 30 seconds,
55° C. for 2 minutes
72° C. for 1 minute

Then, the reaction mixture was diluted 100 times, and newly added with the primer C2 and the primer XDH1-S2 or the primer XDH2-S2, and the second PCR was performed. The conditions were the same as those of the first PCR. The nucleotide sequences of the primer C2, the primer XDH1-S2, and the primer XDH2-S2 are shown as SEQ ID NO: 12, SEQ ID NO: 8, and SEQ ID NO: 10 in Sequence Listing, respectively. The primer C2 was contained in the TaKaRa LA PCR in vitro Cloning Kit, and had the sequence corresponding to the sequence in the PstI cassette and the HindIII cassette. The primer XDH1-S2 and the primer XDH2-S2 each contained a sequence designed based on the amino acid sequences determined, the sequence corresponding to EcoRI site, and EcoRI site.

After the reaction, 3 μl of the reaction mixture was subjected to 0.8% agarose gel electrophoresis. As a result, it was confirmed that a DNA fragment of about 1 kb was amplified when primer XDH1-S2 was used, and a DNA fragment of about 1.7 kb was amplified when XDH2-S2 was used.

(4) Cloning of DNA Fragments Amplified by PCR into pUC19

Cloning was performed by ligating the DNA fragments of about 1 kbp (XDH1) and about 1.7 kbp (XDH2) amplified by PCR with pUC19. The ligation was performed by using DNA Ligation Kit Ver.2 (supplied by Takara Shuzo Co., Ltd.). The experiments were performed according to the instruction attached to the kit hereafter unless otherwise indicated.

400 ng of the DNA fragment of about 1 kb, which had been amplified by using the primer XDH1-S2, was digested with PstI and EcoRI, then purified, and ligated to pUC19 digested with PstI and EcoRI. *Escherichia coli* JM109 was transformed by using this ligation reaction mixture.

Further, 400 ng of the DNA fragment of about 1.7 kb, which had been amplified by using the primer XDH2-S2, was digested with HindIII and EcoRI, then purified, and ligated to pUC19 digested with HindIII and EcoRI. *Escherichia coli* JM109 was transformed by using this ligation reaction mixture.

From the obtained transformant cells, several JM109 strains transformed with pUC19 and containing the target DNA fragment of about 1 kbp (XDH1) or about 1.7 kbp (XDH2) were selected for each case. The selection was performed according to the method described in Molecular Cloning, 2nd edition, Cold Spring Harbor Press (1989).

(5) Determination of Nucleotide Sequence of XDH2 Gene Fragment

The plasmid carried by JM109 transformed with pUC19 containing the DNA fragment of about 1.7 kbp (XDH2) was prepared according to the method described in Molecular Cloning, 2nd edition, Cold Spring Harbor Press (1989), and the nucleotide sequence of the inserted DNA fragment was determined. The sequencing reaction was performed by using Dye Terminator Cycle Sequencing Kit (produced by ABI) according to the instruction attached to the kit. The electrophoresis was performed by using DNA Sequencer 373 (produced by ABI).

As a result, it was found that the DNA fragment amplified by PCR had a sequence of from the thymidine residue at position 1116 to the thymidine residue at position 2774 of the nucleotide sequence shown as SEQ ID NO: 5 in Sequence Listing.

(6) Preparation of DNA Fragment of Upstream Region of XDH2 Gene by PCR

The XDH2 gene and a DNA fragment of the upstream region of the XDH2 gene were amplified and isolated by PCR using the nucleotide sequences determined above. The PCR reaction was performed by using TaKaRa LA PCR in vitro Cloning Kit (supplied by Takara Shuzo Co., Ltd.). The experiments were performed according to the instruction attached to the kit hereafter unless otherwise indicated.

Five µg of the chromosome DNA prepared as in the above (2) was digested with restriction enzyme SalI. Then, SalI cassette was ligated to the DNA fragment collected by ethanol precipitation. Ethanol precipitation was further performed, and first PCR was performed for the collected DNA by using the primer C1 and the primer XDH2UP-S1. The nucleotide sequences of the primer C1 and the primer XDH2UP-S1 are shown as SEQ ID NO: 11 and SEQ ID NO: 13 in Sequence Listing, respectively. The primer XDH2UP-S1 is a sequence complementary to the region of from the cytosine residue at position 1317 to the cytosine residue at position 1283 of the nucleotide sequence of the gene cluster coding for XDH2 of *Gluconobacter* shown as SEQ ID NO: 5.

The PCR reaction was performed by using Gene Amp PCR System 9600 (produced by PERKIN ELMER), and a reaction according to the following conditions was repeated for 30 cycles.

94° C. for 30 seconds,
55° C. for 2 minutes
72° C. for 1 minute

Then, the reaction mixture was diluted 100 times, and newly added with the primer C2 and the primer XDH2UP-S2 to perform the second PCR. The conditions were the same as those of the first PCR. The sequences of the primer C2 and the primer XDH2UP-S2 are shown as SEQ ID NO: 12 and SEQ ID NO: 14 in Sequence Listing, respectively. The primer XDH2UP-S2 is composed of a sequence complementary to the region of from the guanosine residue at position 1255 to the guanosine residue at position 1225 of the nucleotide sequence of the gene coding for XDH2 of *Gluconobacter* shown as SEQ ID NO: 5. After the reaction, 3 µl of the reaction mixtures was subjected to 0.8% agarose gel electrophoresis. As a result, it was confirmed that a DNA fragment of about 1.3 kb had been amplified.

(7) Determination of Nucleotide Sequence of XDH2 Gene and DNA Fragment Containing Upstream Region Thereof The DNA fragment of about 1.3 kbp amplified by the aforementioned PCR was purified, and determined for the nucleotide sequence. The sequencing reaction was performed by using Dye Terminator Cycle Sequencing Kit (produced by ABI) according to the instruction attached to the kit. The electrophoresis was performed by using DNA Sequencer 373 (produced by ABI).

As a result, it was found that the DNA fragment amplified in the above (6) had a sequence from the guanosine residue at position 1 to the guanosine residue at position 1224 of the nucleotide sequence shown as SEQ ID NO: 5 in Sequence Listing. The nucleotide sequence shown in SEQ ID NO: 5 comprises this nucleotide sequence combined with the nucleotide sequence determined in the above (5). The amino acid sequence which may be encoded by this nucleotide sequence, deduced based on the universal codons, is shown together in SEQ ID NO: 5, and also shown as SEQ ID NO: 6. The sequence of from 2nd to 26th amino acid residues of that amino acid sequence completely corresponded to the sequence of the 1st to the 25th amino acid residues of the N-terminus amino acid sequence of XDH2 shown as SEQ ID NO: 2. From this, it was confirmed that the DNA fragments amplified by the PCR were the target XDH2 gene and its upstream region derived from *Gluconobacter* bacteria.

(8) Cloning of DNA Fragment Containing Full Length XDH2 Gene Coding Region

Cloning was performed by amplifying a DNA fragment containing full length XDH2 gene coding region by PCR, and ligating it to pUC18. The PCR reaction was performed by using TaKaRa LAPCR kit (supplied by Takara Shuzo Co., Ltd.). The experiments were performed according to the instruction attached to the kit hereafter unless otherwise indicated.

PCR was performed by using 1 µg of chromosome DNA of *Gluconobacter oxydans* ATCC621 strain produced in the same manner as in the above (2) as template, and using a primer XDH2-5' and a primer XDH2-3'. The nucleotide sequence of the primer XDH2-5' was shown as SEQ ID NO: 15, and the nucleotide sequence of the primer XDH2-3' was shown as SEQ ID NO: 16 in Sequence Listing. The primer XDH2-5' comprises a sequence corresponding to the region from the cytosine residue at position 1043 to the adenosine residue at position 1063 of the nucleotide sequence containing the XDH2 gene shown as SEQ ID NO: 5, and the primer XDH2-3' comprises a sequence complementary to the region from the guanosine residue at position 1957 to the cytosine residue at position 1978 of the same.

The PCR reaction was performed by using GeneAmp PCR System 9600 (produced by PERKIN ELMER), and a reaction according to the following conditions was repeated for 30 cycles.

94° C. for 30 seconds,
55° C. for 2 minutes
72° C. for 1 minute

After the reaction, 3 µl of the reaction mixture was subjected to 0.8% agarose gel electrophoresis. As a result, it was confirmed that a DNA fragment of about 1 kbp had been amplified.

The DNA fragment of about 1 kbp amplified by the aforementioned PCR was ligated to pUC18 to perform cloning. The cloning was performed by using DNA Ligation Kit Ver.2 (supplied by Takara Shuzo Co., Ltd.). The experiments were performed according to the instruction attached to the kit hereafter unless otherwise indicated. 400 ng of the amplified DNA fragment of about 1 kb was digested with BamHI and EcoRI, then purified, and ligated to pUC18 digested with BamHI and EcoRI. *Escherichia coli* JM109 was transformed by using this ligation reaction mixture.

From the obtained transformants, several JM109 strains transformed with pUC18 containing the target DNA fragment of about 1 kbp were selected. The selection was performed according to the method described in Molecular Cloning, 2nd edition, Cold Spring Harbor Press (1989).

The XDH2 gene derived form *Gluconobacter oxydans* could be cloned as described above. The plasmid having the target XDH2 gene fragment obtained by the aforementioned method is referred to as pUCXDH2.

(9) Determination of Nucleotide Sequence of XDH1 Gene Fragment

The plasmid carried by the JM109 strains transformed with pUC18 containing the DNA fragment of about 1 kbp (XDH1) and selected above (4) was extracted according to the method described in Molecular Cloning, 2nd edition, Cold Spring Harbor Press (1989), and the nucleotide sequence of the inserted DNA fragment was determined. The sequencing reaction was performed by using Dye Terminator Cycle Sequencing Kit (produced by ABI) according to the instruction attached to the kit. The electrophoresis was performed by using DNA Sequencer 373 (produced by ABI).

As a result, it was found that the DNA fragment amplified by PCR had a sequence from the guanosine residue at position 52 to the guanosine residue at position 1011 of the nucleotide sequence shown as SEQ ID NO: 3 in Sequence Listing.

(10) Cloning of XDH1 Gene from Chromosome DNA Library i) Construction of Chromosome DNA Library One µg of the chromosome DNA prepared in the above (2) was completely digested with HindIII. After the DNA was collected by ethanol precipitation, it was dissolved in 10 µl of 10:1 TE. Five µg of this solution and 1 ng of pUC19 (supplied by Takara Shuzo Co., Ltd.) which had been digested with HindIII and subjected to dephosphorylation with BAP (bacterial alkaline phosphatase) were mixed, and the ligation reaction was performed by using DNA Ligation Kit Ver.2 (supplied by Takara Shuzo Co., Ltd.). Three µl of this ligation reaction mixture was mixed with 100 µl of competent cells of *Escherichia coli* JM109 strain (supplied by Takara Shuzo Co., Ltd.) to transform the *Escherichia coli* JM109 strain. This was applied on a suitable solid medium to create a chromosome DNA library.

ii) Preparation of Probe

It was decided to use a part of the XDH1 gene obtained in the above (3) for a probe. The DNA fragment of about 1 kb amplified by using the primer C2 and the primer XDH1-S2, which was obtained in the above (3), was separated by 1% agarose gel electrophoresis. The target band was excised, and the DNA was purified by using Gene Clean II Kit (produced by Funakoshi). Finally, 16 µl of 50 ng/µl DNA solution was obtained. A probe labeled with digoxigenin was obtained by using this DNA fragment and DIG High Prime (produced by Boehringer Mannheim) according to the instruction attached to the product.

iii) Screening by Colony Hybridization

In order to obtain the XDH1 gene in full length, screening of the chromosome DNA library by colony hybridization utilizing the aforementioned probe was performed. The colony hybridization was performed according to the method described in Molecular Cloning, 2nd edition, Cold Spring Harbor Press (1989).

The colonies of the chromosome DNA library were blotted to a nylon membrane filter (Hybond-N produced by Amersham), denatured with alkali, neutralized, and immobilized. Hybridization was performed by using EASY HYB (produced by Boehringer Mannheim). The filter was immersed into the buffer (EASY HYB), and pre-hybridization was performed at 42° C. for one hour. Then, the labeled probe produced above was added, and hybridization was performed at 42° C. for 16 hours. Then, the filter was washed with 2×SSC containing 0.1% SDS at room temperature for 20 minutes. Further, it was washed twice with 0.1×SSC containing 0.1% SDS at 65° C. for 15 minutes.

The colonies hybridizable with the probe was detected by using DIG Nucleotide Detection Kit (produced by Boehringer Mannheim) according to the instruction attached to the kit. As a result, four strains of colonies hybridizable with the probe could be confirmed.

(11) DNA Sequence of XDH1 Gene

In the same manner as in the above (5), the nucleotide sequence of the DNA fragment inserted into pUC19 was determined. The result is shown as SEQ ID NO: 3 in Sequence Listing. The amino acid sequence, which is deduced to be encoded by the nucleotide sequence based on universal codons, is shown in SEQ ID NO: 3 together with the nucleotide sequence, and also shown as SEQ ID NO: 4. The amino acid sequence from the 2nd to 28th amino acid residues completely corresponded to the sequence composed of the 27 residues of the 1st to the 27th amino acid residues of the sequence shown as SEQ ID NO: 1. From this, it was confirmed that the obtained DNA fragment was the target XDH1 gene derived from *Gluconobacter* bacteria and flanking regions thereof.

EXAMPLE 4

Expression of XDH2 Gene Derived from *Gluconobacter* Bacteria in *Escherichia coli* and Purification of the Product <1> Culture of *Escherichia coli* Harboring Recombinant XDH2 Gene and Induction of Expression In the pUCXDH2 obtained in Example 3, the DNA coding for XDH2 gene derived from *Gluconobacter* bacteria is ligated downstream of lacZ promoter, and therefore it was designed to be expressed under the control of lacZ promoter.

*Escherichia coli* JM109 transformed with pUCXDH2, and *Escherichia coli* JM109 transformed with pUC18 as a control were cultured at 37° C. overnight with shaking in 50 ml of LB medium containing 100 µg/ml of ampicillin. These were used as seed culture. The seed culture of *Escherichia coli* JM109 transformed with pUCXDH2 was inoculated in an amount of 1% to a flask containing fresh medium, and this was designated as Experimental panel 1. On the other hand, the seed culture of *Escherichia coli* JM109 transformed with pUC18 was similarly inoculated in an amount of 1% to a flask, and this was designated as Experimental panel 2 (control). Each experimental panel was cultured, and when absorbance of the culture for a light having a wavelength of 610 nm became about 0.7, it was added with IPTG (isopropyl-beta-D-thiogalactopyranoside) to a final concentration of 1 mM. Then, after 4 hours, the culture was completed.

<2> Confirmation of Protein Obtained by Induced Expression

After the completion of the cultivation, the cells were collected by centrifugation (12,000×g, 15 minutes) of 10 ml of the culture broth. The cells were suspended in 2 ml of 10 mM Tris-HCl, pH 7.5, washed and recovered by centrifugation. The cells were suspended in 1 ml of the same buffer, and disrupted by shaking with 0.1 mm zirconia beads for 3 minutes using Multi Beads Shocker (Yasui Kikai). This disrupted cell suspension was subjected to SDS-PAGE, and stained with CBB (Coomassie Brilliant Blue). As a result, a band corresponding to a molecular weight of about 27,000 to 30,000 was confirmed, which was observed only in Experimental panel 1 (JM109 transformed with pUCXDH2). Deduced from the molecular weight, it was considered that the desired XDH2 protein was expressed.

<3> Confirmation of XDH Activity

The XDH activity of the expressed protein was measured. The XDH activity was measured by using the aforementioned disrupted cell suspension according to the method described in Example 1. As a result, 14 U/mg of the XDH activity was detected in the *Escherichia coli* JM109 transformed with pUCXDH2, whereas no XDH activity was detected in the *Escherichia coli* JM109 transformed with pUC18 as the control. From this result, it was confirmed that *Escherichia coli* JM109 transformed with pUCXDH2 showed the XDH activity.

<4> Purification of XDH2 from Recombinant *Escherichia coli* JM109

The *Escherichia coli* JM109 cells transformed with pUCXDH2, which were cultured in the above <2>, were collected by centrifugation. The obtained cells were used as a material for purification of XDH. The XDH activity was measured by the method described in Example 1.

(1) Preparation of Cell Extract

The above bacterial cells were suspended in 50 mM potassium phosphate buffer (pH 7), and collected again in a precipitated fraction obtained by centrifugation at 5000×g for 10 minutes. This procedure comprising suspension and centrifugation was performed as washing of the cells. This washing process of the cells was repeated twice.

Three grams of the washed cells was suspended in 20 ml of Buffer 1 (20 mM Tris-HCl (pH 7.6), 0.5 mM EDTA, 1 mM MgCl$_2$, 1 mM DTT), and disrupted by sonication for 20 minutes at 4° C. The disrupted suspension was centrifuged (8000 rpm, 10 minutes) to remove cell residues, and ultracentrifuged (56000 rpm, 30 minutes) to remove insoluble fraction.

(2) Anion Exchange Chromatography

The obtained soluble fraction was loaded on an anion exchange chromatography column Q-Sepharose FF (produced by Pharmacia) equilibrated by Buffer 1. By this operation, XDH was adsorbed on the carrier.

The protein not adsorbed on the carrier (non-adsorbed protein) was washed off by using Buffer 1, and then the adsorbed protein was eluted by using a buffer containing KCl as an eluate. In this elution, KCl concentration in the buffer was linearly changed from 0 M to 0.5 M. The XDH activity was measured for each eluted fraction obtained by this elution, and the XDH activity was found in eluted fractions corresponding to the KCl concentration of about 200 to 350 mM.

(3) NAD Affinity Chromatography

The above-obtained fractions containing the XDH activity were combined, and dialyzed against Buffer 1. The solution after the dialysis was filtered through a 0.45 μm filter. The obtained filtrate was loaded on an NAD affinity column HiTrap Blue 5 ml (produced by Pharmacia) equilibrated with Buffer 1. By this operation, XDH was adsorbed on the carrier. Then, the protein not adsorbed on the carrier (non-adsorbed protein) was washed off by using Buffer 1, and then the adsorbed protein was eluted by using, as an eluate, Buffer 2 (20 mM Tris-HCl (pH 7.6), 0.5 mM EDTA, 1 mM MgCl$_2$, 1 mM DTT, 5 mM NAD) containing NAD. As a result, XDH was detected in the eluted fractions.

(4) Hydrophobic Chromatography

The eluted fractions for which the activity was detected were dialyzed against Buffer 3 (50 mM potassium phosphate buffer, 1 M ammonium sulfate, pH 7.0). The solution obtained after the dialysis was filtered through a 0.45 μm filter. The obtained filtrate was loaded on a hydrophobic chromatography column Phenyl Sepharose HP (produced by Pharmacia) equilibrated with Buffer 3. By this operation, XDH was adsorbed on the carrier.

Then, the protein not adsorbed on the carrier was washed off by using Buffer 3, and then the adsorbed protein was eluted by using Buffer 4 (50 mM potassium phosphate buffer, pH 7.0) as an eluate. For this elution, ammonium sulfate concentration in the buffer was linearly changed from 1 M to 0 M. The XDH activity was measured for each eluted fraction obtained by this elution, and the XDH activity was found in eluted fractions corresponding to the ammonium sulfate concentration of about 200 to 300 mM.

The obtained active fraction was subjected to SDS-PAGE, and stained with Coomassie Brilliant Blue. As a result, it was confirmed that XDH2 had been purified to such a level that XDH2 could be detected as a single band, and its molecular weight was estimated to be about 27,000 to abut 30,000. That is, XDH2 expressed in *Escherichia coli* JM109 could be purified as a single enzyme.

EXAMPLE 5

Determination of Optimum pH of XDH

By using the XDH2 enzyme obtained in Example 4, variation of the enzyme activity depending on the reaction pH was measured as follows to determine the optimum pH.

Sodium acetate buffers (pH 3.3, 4, 4.5, 5 and 6), Tris-HCl (pH 7 and 8), Glycine-NaOH (pH 9), and CAPS-NaOH (pH 10) buffers were used for the enzyme reaction buffers. Measurement of the XDH activity for the reduction reaction was performed as follows. Thirty μl of an enzyme solution was added to 570 μl of a reaction solution containing 100 mM (final concentration) D-xylulose, 0.2 mM NADH, and 100 mM buffer to allow the enzymatic reaction at 30° C., and the decrease of NADH caused by the reaction was determined by measuring the absorbance at 340 nm using a spectrophotometer (DU 640 Spectrometer produced by BECKMAN). The activity decreasing 1 μmol of NADH per minute was defined as 1 U. The calculation was performed by using the molecular extinction coefficient ε of NADH at 340 nm of $6.3 \times 10^3$. Each buffer was added so that it should have a concentration of 100 mM in the reaction solution. The XDH fraction purified above was used as an enzyme source, and the reaction was performed at 30° C. The result of the measurement was represented as a relative value of enzyme activity to the actually determined pH value of each reaction solution. For convenience, the activity for the oxidation reaction at pH 5 was defined as 100. The results of the measurement are shown in FIG. 2.

Figure 2:
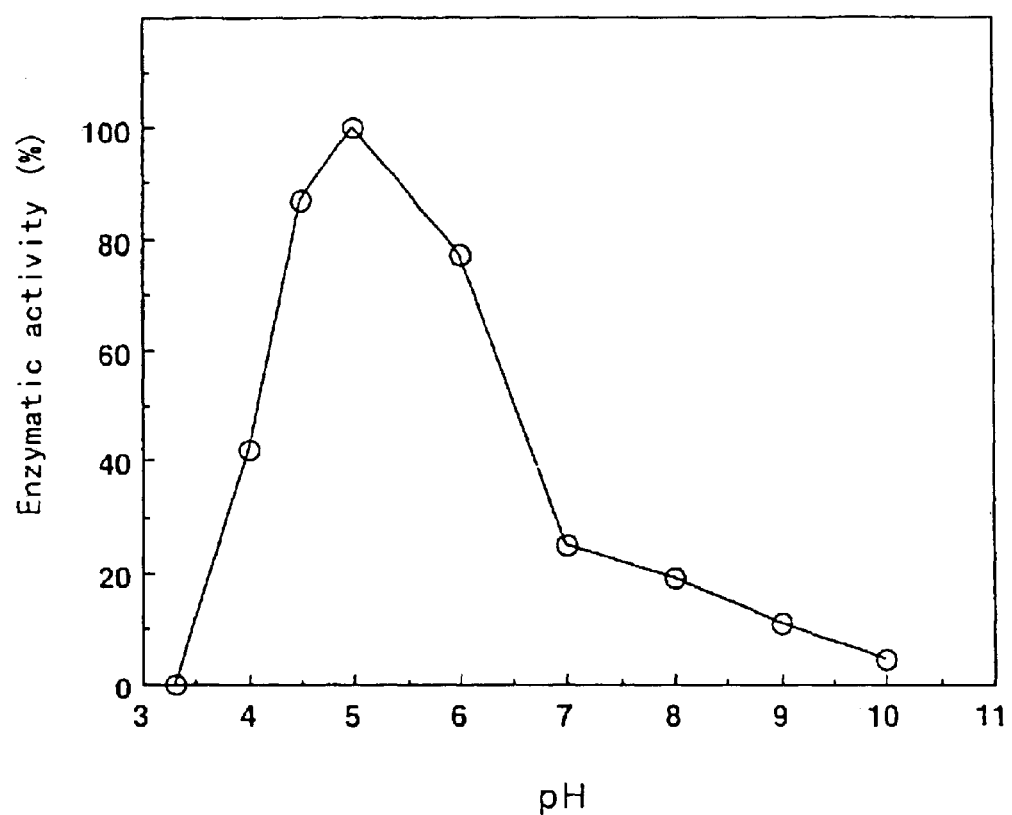
FIG. 2 is a graph representing the pH dependency of the enzyme activity of XDH2.

It was found that the optimum pH for the reduction reaction (reaction producing xylitol from D-xylulose) of the XDH2 of the present invention was about 5 (see FIG. 2). Since the optimum pH for the reduction reaction of the XDH derived from *Asperhillus niger* reported by Cor F. B. Witteveen, et al. (*Microbiology,* 140, 1679–1685, 1994) is strictly 6.5, and therefore the XDH2 of the present invention derived from *Gluconobacter* bacteria is clearly different from the known XDH in the reaction optimum pH. That is, it was demonstrated that, among the *Gluconobacter* bacteria derived XDH found by the present invention, at least XDH2 was characterized in that it had a lower optimum pH for the reduction reaction.

What is claimed is:

1. An isolated DNA defined in the following (c) or (d):
   (c) a DNA comprising at least a nucleotide sequence corresponding to nucleotide numbers 1063 to 1848 of the nucleotide sequence of SEQ ID NO: 5;
   (d) a DNA which contains at least a nucleotide sequence corresponding to nucleotide numbers 1063 to 1848 of the nucleotide sequence of SEQ ID NO: 5 or a probe prepared from the nucleotide sequence under stringent conditions in which washing is performed at 60° C. and at a salt concentration corresponding to 1×SSC and 0.1% SDS, and which codes for a protein having xylitol dehydrogenase activity.

2. The DNA of claim 1, which codes for (c).

3. The DNA of claim 1, which codes for (d).

4. An isolated DNA which codes for a protein defined in the following (C) or (E):
   (C) a protein which has the amino acid sequence of SEQ ID NO: 6;
   (E) a protein which has the amino acid sequence of SEQ ID NO: 6 including substitution, deletion, insertion or addition of 1 to 10 amino acids, and has xylitol dehydrogenase activity.

5. The DNA of claim 4, which codes for (E).

6. A cell into which the DNA of claim 1 has been introduced.

7. A cell into which the DNA of claim 2 has been introduced.

8. A cell into which the DNA of claim 3 has been introduced.

9. A cell into which the DNA of claim 4 has been introduced.

10. A cell into which the DNA of claim 5 has been introduced.

11. A method for producing xylilol dehydrogenase, comprising cultivating the cell of claim 4 in a suitable medium for a time and under conditions suitable for production of xylitol dehydrogenase.

12. The method of claim 11, further comprising collecting the xylitol dehydrogenase from the culture medium.

* * * * *

SEQUENCE LISTING

```
<160> NUMBER OF SEQ ID NOS: 16

<210> SEQ ID NO 1
<211> LENGTH: 26
<212> TYPE: PRT
<213> ORGANISM: Gluconobacter oxydans

<400> SEQUENCE: 1

Ala Asp Thr Leu Ala Ala Val Val Arg Glu Phe Gly Lys Pro Leu Ser
1               5                   10                  15

Ile Glu Arg Leu Pro Ile Pro Asp Ile Lys
            20                  25

<210> SEQ ID NO 2
<211> LENGTH: 25
<212> TYPE: PRT
<213> ORGANISM: Gluconobacter oxydans

<400> SEQUENCE: 2

Ser Lys Lys Phe Asn Gly Lys Val Cys Leu Val Thr Gly Ala Gly Gly
1               5                   10                  15

Asn Ile Gly Leu Ala Thr Ala Leu Arg
            20                  25

<210> SEQ ID NO 3
<211> LENGTH: 1056
<212> TYPE: DNA
<213> ORGANISM: Gluconobacter oxydans
<220> FEATURE:
<221> NAME/KEY: CDS
<222> LOCATION: (25)..(1053)

<400> SEQUENCE: 3
cacccgccag aaggagtctt ttcc atg gct gat aca atg ctc gcc gcc gtc        51
                           Met Ala Asp Thr Met Leu Ala Ala Val
                             1               5 gtc cgt gaa ttc ggc aag ccg ctc tcc atc gag cgg cta ccc atc ccg        99
Val Arg Glu Phe Gly Lys Pro Leu Ser Ile Glu Arg Leu Pro Ile Pro
 10              15                  20                  25 gac atc aag ccc cac cag atc ctc gtg aag gtc gat acc tgt ggc gtc       147
Asp Ile Lys Pro His Gln Ile Leu Val Lys Val Asp Thr Cys Gly Val
                 30                  35                  40 tgc cac act gac ctg cac gcc gcg cgc ggg gac tgg ccg tcc aag ccc       195
Cys His Thr Asp Leu His Ala Ala Arg Gly Asp Trp Pro Ser Lys Pro
             45                  50                  55 aac ccg ccg ttc att ccc ggg cat gaa ggc gtc gga cac atc gtc gcc       243
Asn Pro Pro Phe Ile Pro Gly His Glu Gly Val Gly His Ile Val Ala
         60                  65                  70 gtc ggc agt cag gtc ggc gat ttc gtc aag acc ggc gat gtc gtg ggc       291
```

|  |  |  |  |  |  |  |  |  |  |  |  |  |  |  |  |
|---|---|---|---|---|---|---|---|---|---|---|---|---|---|---|---|
| Val | Gly | Ser | Gln | Val | Gly | Asp | Phe | Val | Lys | Thr | Gly | Asp | Val | Val | Gly |
|  | 75 |  |  |  | 80 |  |  |  |  | 85 |  |  |  |  |  |

```
gtg ccc tgg ctc tac tcc gcc tgc ggt cac tgc gaa cac tgt ctg ggc      339
Val Pro Trp Leu Tyr Ser Ala Cys Gly His Cys Glu His Cys Leu Gly
90              95                  100                 105 ggc tgg gaa aca ctc tgc gaa aag cag gac gac acc ggc tac acc gtc      387
Gly Trp Glu Thr Leu Cys Glu Lys Gln Asp Asp Thr Gly Tyr Thr Val
                    110                 115                 120 aat ggc tgc ttc gcc gaa tat gtc gtg gca gac ccg aac tac gtc gca      435
Asn Gly Cys Phe Ala Glu Tyr Val Val Ala Asp Pro Asn Tyr Val Ala
            125                 130                 135 cac ctg ccc tcg acc atc gac ccg ctt cag gcc tcg ccg gtc ctg tgc      483
His Leu Pro Ser Thr Ile Asp Pro Leu Gln Ala Ser Pro Val Leu Cys
        140                 145                 150 gcg ggg ctg acg gtc tat aag ggc ctg aaa atg acg gag gcc cgc ccc      531
Ala Gly Leu Thr Val Tyr Lys Gly Leu Lys Met Thr Glu Ala Arg Pro
    155                 160                 165 ggc cag tgg gtc gca gtc tcg ggc gtc ggc ggt ctc ggc cag atg gcc      579
Gly Gln Trp Val Ala Val Ser Gly Val Gly Gly Leu Gly Gln Met Ala
170             175                 180                 185 gtg cag tac gcc gtc gcc atg ggc atg aat gtc gtc gcg gtg gac atc      627
Val Gln Tyr Ala Val Ala Met Gly Met Asn Val Val Ala Val Asp Ile
                190                 195                 200 gat gac gaa aaa ctc gcc aca gcc aaa aag ctc ggc gca tcc ctg acc      675
Asp Asp Glu Lys Leu Ala Thr Ala Lys Lys Leu Gly Ala Ser Leu Thr
            205                 210                 215 gtc aac gcc aag gac acg gac ccg gcc agg ttc atc cag cag cag atc      723
Val Asn Ala Lys Asp Thr Asp Pro Ala Arg Phe Ile Gln Gln Gln Ile
        220                 225                 230 ggc ggc gca cat ggc gct ctc gtc acc gct gtc gga cgg acg gcg ttt      771
Gly Gly Ala His Gly Ala Leu Val Thr Ala Val Gly Arg Thr Ala Phe
    235                 240                 245 tcg cag gcc atg ggc tat gcc cgc cgc ggc ggc acc atc gtc ctg aac      819
Ser Gln Ala Met Gly Tyr Ala Arg Arg Gly Gly Thr Ile Val Leu Asn
250             255                 260                 265 gga ctg ccg ccc ggc gat ttc ccg gtc tcg atc ttc gac atg gtc atg      867
Gly Leu Pro Pro Gly Asp Phe Pro Val Ser Ile Phe Asp Met Val Met
                270                 275                 280 aac ggc acc acc atc cgt ggc tcc atc gtc gga aca cgg ctg gac atg      915
Asn Gly Thr Thr Ile Arg Gly Ser Ile Val Gly Thr Arg Leu Asp Met
            285                 290                 295 atc gag gcc atg gat ttc ttc gcc cgc ggc aag gtc aaa tcc gtc gtc      963
Ile Glu Ala Met Asp Phe Phe Ala Arg Gly Lys Val Lys Ser Val Val
        300                 305                 310 acc ccc gga aaa ctt gaa aac atc aat acg atc ttc gac gat ctg cag     1011
Thr Pro Gly Lys Leu Glu Asn Ile Asn Thr Ile Phe Asp Asp Leu Gln
    315                 320                 325 aat ggt cgc ctc gaa ggc cgg aca gtg ctc gac ttc cgg tcc tga         1056
Asn Gly Arg Leu Glu Gly Arg Thr Val Leu Asp Phe Arg Ser
330             335                 340

<210> SEQ ID NO 4
<211> LENGTH: 343
<212> TYPE: PRT
<213> ORGANISM: Gluconobacter oxydans

<400> SEQUENCE: 4

Met Ala Asp Thr Met Leu Ala Ala Val Val Arg Glu Phe Gly Lys Pro
1               5                   10                  15

Leu Ser Ile Glu Arg Leu Pro Ile Pro Asp Ile Lys Pro His Gln Ile
```

|          |     | 20  |     |     |     | 25  |     |     |     | 30  |     |     |
|----------|-----|-----|-----|-----|-----|-----|-----|-----|-----|-----|-----|-----|
| Leu | Val | Lys | Val | Asp | Thr | Cys | Gly | Val | Cys | His | Thr | Asp | Leu | His | Ala |
|     |     |     | 35  |     |     |     |     | 40  |     |     |     |     | 45  |     |     |

Leu Val Lys Val Asp Thr Cys Gly Val Cys His Thr Asp Leu His Ala
                35                    40                  45

Ala Arg Gly Asp Trp Pro Ser Lys Pro Asn Pro Pro Phe Ile Pro Gly
 50                      55                  60

His Glu Gly Val Gly His Ile Val Ala Val Gly Ser Gln Val Gly Asp
 65                  70                  75                  80

Phe Val Lys Thr Gly Asp Val Val Gly Val Pro Trp Leu Tyr Ser Ala
                 85                  90                  95

Cys Gly His Cys Glu His Cys Leu Gly Gly Trp Glu Thr Leu Cys Glu
             100                 105                 110

Lys Gln Asp Asp Thr Gly Tyr Thr Val Asn Gly Cys Phe Ala Glu Tyr
             115                 120                 125

Val Val Ala Asp Pro Asn Tyr Val Ala His Leu Pro Ser Thr Ile Asp
 130                 135                 140

Pro Leu Gln Ala Ser Pro Val Leu Cys Ala Gly Leu Thr Val Tyr Lys
145                 150                 155                 160

Gly Leu Lys Met Thr Glu Ala Arg Pro Gly Gln Trp Val Ala Val Ser
                 165                 170                 175

Gly Val Gly Gly Leu Gly Gln Met Ala Val Gln Tyr Ala Val Ala Met
             180                 185                 190

Gly Met Asn Val Val Ala Val Asp Ile Asp Glu Lys Leu Ala Thr
             195                 200                 205

Ala Lys Lys Leu Gly Ala Ser Leu Thr Val Asn Ala Lys Asp Thr Asp
 210                 215                 220

Pro Ala Arg Phe Ile Gln Gln Ile Gly Gly Ala His Gly Ala Leu
225                 230                 235                 240

Val Thr Ala Val Gly Arg Thr Ala Phe Ser Gln Ala Met Gly Tyr Ala
                 245                 250                 255

Arg Arg Gly Gly Thr Ile Val Leu Asn Gly Leu Pro Pro Gly Asp Phe
             260                 265                 270

Pro Val Ser Ile Phe Asp Met Val Met Asn Gly Thr Thr Ile Arg Gly
             275                 280                 285

Ser Ile Val Gly Thr Arg Leu Asp Met Ile Glu Ala Met Asp Phe Phe
290                 295                 300

Ala Arg Gly Lys Val Lys Ser Val Val Thr Pro Gly Lys Leu Glu Asn
305                 310                 315                 320

Ile Asn Thr Ile Phe Asp Leu Gln Asn Gly Arg Leu Glu Gly Arg
             325                 330                 335

Thr Val Leu Asp Phe Arg Ser
             340

<210> SEQ ID NO 5
<211> LENGTH: 2774
<212> TYPE: DNA
<213> ORGANISM: Gluconobacter oxydans
<220> FEATURE:
<221> NAME/KEY: CDS
<222> LOCATION: (1063)..(1848)

<400> SEQUENCE: 5
gcgcaatgat cttgcgaccc gtcaggccgg cgtcgccgtc cggtccgccg atgacgaagt      60
taccggtcgg gttcacgtag aactcgtctt ccgggcaggt ccagccttcc ggcaggatgc     120
cgttgaccac gtcgcgcagg gtttcgccgg atcgtgttct ggctcatgcc ctcgacatgc     180

-continued

```
tgcgtggaaa tcacgacgga cgtgacgcca accggcttgc catcgacata acgcagcgtg    240
acctggctct tggcatccgg cagaaggccg acgccacggg cgtcgccgtt cttgcggtag    300
tcgcggatgc gctcgaggat cgtctgcgcg taatacagcg gcgcaggcat caggtgttcg    360
gtttcgcgcg tggcgtagcc gaacatgatg ccctggtcac cagcgccctc gtccttgtcg    420
ctgccgctgt caacgccctg ggcgatgtcg gcggactgtg cgtgcaggta ggaggtgatg    480
tcggccttct tccaggagaa accttcctgg tcgtagccga tgtccttgat ggcttcacgg    540
gcacggtcga tcagcgtgtc ctcgacctct ttggggccgc ggacttcacc ggccaggatg    600
acgcggttgg tggtgaccag cgtctcacag gcaacacgtg cttccggatc ggcctgcaga    660
taggcgtcca gaacggtatc ggaaatgcgg tccgccacct tgtcgggatg gccctcggaa    720
acggactcga acgtgaaaag gaaatcgccg tgattgcgca ctcagggacc tgcagggaa    780 tgagtggtga aagggccac agggtgtctt ggcagacagg ctgtggcatt cagggaggtg    840
acggcttggc ggaattggtc gcaagggtca agggcgtgca tggggtctga acgcggtttt    900
ctgcgggaaa gtcccgaaaa ccgccgtgag atcacaaaaa agagagccgg cgccccgtt    960 tcatttttca acgacaccgt ccatgctgcg ttcgtgttcc cgcgacccct gttgcccgtc    1020
acgggtgcgg tcccgggaaa aacagagttt gaggcattcg ga atg tcg aag aag      1074
                                                 Met Ser Lys Lys
                                                   1 ttt aac ggt aaa gtc tgt ctg gtc acc ggc gcg ggt ggc aat atc ggt     1122
Phe Asn Gly Lys Val Cys Leu Val Thr Gly Ala Gly Gly Asn Ile Gly
 5              10                  15                  20 ctt gcg acc gcc ctc cgt ctg gca gaa gag ggc acg gcc atc gcc ctt     1170
Leu Ala Thr Ala Leu Arg Leu Ala Glu Glu Gly Thr Ala Ile Ala Leu
             25                  30                  35 ctg gac atg aac cgc gag gcg ctg gaa aag gcg gaa gcc tcc gtc cgt     1218
Leu Asp Met Asn Arg Glu Ala Leu Glu Lys Ala Glu Ala Ser Val Arg
         40                  45                  50 gaa aag ggc gtc gaa gcc cgc tcc tat gtc tgt gac gtc acg tcc gaa     1266
Glu Lys Gly Val Glu Ala Arg Ser Tyr Val Cys Asp Val Thr Ser Glu
     55                  60                  65 gag gcc gtg atc ggg acg gtg gat agc gtg gtc cgg gac ttc ggg aag     1314
Glu Ala Val Ile Gly Thr Val Asp Ser Val Val Arg Asp Phe Gly Lys
 70                  75                  80 atc gac ttc ctg ttc aac aat gcc ggc tat cag ggc gcc ttc gcc ccc     1362
Ile Asp Phe Leu Phe Asn Asn Ala Gly Tyr Gln Gly Ala Phe Ala Pro
 85              90                  95                 100 gtg cag gac tac ccg tcc gac gat ttc gcg cgc gtg ctg acg atc aac     1410
Val Gln Asp Tyr Pro Ser Asp Asp Phe Ala Arg Val Leu Thr Ile Asn
            105                 110                 115 gtc acc ggt gcc ttc cac gtc ctc aaa gcc gtt tcg cgc cag atg atc     1458
Val Thr Gly Ala Phe His Val Leu Lys Ala Val Ser Arg Gln Met Ile
        120                 125                 130 acg cag aac tac ggg cgc atc gtc aac acc gcc agc atg gcc ggt gtg     1506
Thr Gln Asn Tyr Gly Arg Ile Val Asn Thr Ala Ser Met Ala Gly Val
    135                 140                 145 aag gga ccg cca aac atg gcc gcc tat ggt gcg tcc aag ggc gcc atc     1554
Lys Gly Pro Pro Asn Met Ala Ala Tyr Gly Ala Ser Lys Gly Ala Ile
150                 155                 160 atc gcc ctg acc gaa acg gcc gcg ctt gac ctt gcc ccc tac aac atc    1602
Ile Ala Leu Thr Glu Thr Ala Ala Leu Asp Leu Ala Pro Tyr Asn Ile
165                 170                 175                 180 cgt gtg aac gcc atc agc ccc ggt tac atg ggg ccc ggt ttc atg tgg    1650
Arg Val Asn Ala Ile Ser Pro Gly Tyr Met Gly Pro Gly Phe Met Trp
                185                 190                 195
```

```
gag cgt cag gtc gag ctt cag gcc aag gtc gga agc cag tat ttc tcc    1698
Glu Arg Gln Val Glu Leu Gln Ala Lys Val Gly Ser Gln Tyr Phe Ser
        200                 205                 210 acc gat ccc aag gtc gtg gcc cag cag atg atc ggc agc gtt ccg atg    1746
Thr Asp Pro Lys Val Val Ala Gln Gln Met Ile Gly Ser Val Pro Met
    215                 220                 225 cgc cgc tat ggc gac atc aac gag atc ccg ggc gta gta gcg ttc ctg    1794
Arg Arg Tyr Gly Asp Ile Asn Glu Ile Pro Gly Val Val Ala Phe Leu
        230                 235                 240 ctg ggg gat gat tcc agc ttc atg acg ggg gtg aac ctg ccg att gct    1842
Leu Gly Asp Asp Ser Ser Phe Met Thr Gly Val Asn Leu Pro Ile Ala
245                 250                 255                 260 ggc ggt tgatcggggg agtccgggct ctgcccgggc ccggcaggga ttttaatccc     1898
Gly Gly tgcaccctgt tttaagttag cgttttaagg cgtcggccat tgtgtagagg ccggcggggc    1958
gtcctgcgag ccatcttgcg gccagcaggg cgcctcttgc gaagaccctg cggtccagtg    2018
cgcggtgcga cagagtgatc tgttcgtctg cggccatcag aacgagatca tgttcgccta    2078
cgatctgtcc gccgcgcagg gaggcgaatc cgatcgcgcc atccggacgt cggccgttct    2138
ggtcggtccg ggccacgtcc tcgaaactga caccacgtcc ttccgccaca gcccggccga    2198
tcgccagtgc cgtgccggac ggcgcgtcca gcttctggcg gtgatgaact tccagaattt    2258
ccgcatcata atccggcagc cctgcaccaa gctgacgggc gagctccaga aacagcgtca    2318
gcgccggtga gaaattggcg gcctgaagaa cgggaatatg ctgcgccgcc gcgttcacgg    2378
catcctgcgc gccctgatcg agccccgtcg tccccagaac ccaggcgcat ccggcctgcg    2438
caaaggctgc cgcatgggcc ggaacggtcg aagcatggct gacatcgatc acgacatcgc    2498 agttttcgc gagtgcggcg ggatcggtgg tgatgttgcg ctgggggtct gctgtccggg     2558
agaggccgcc gacgagggca gaaccagcct cttcggcaca aagcgttcca agccggcccg    2618
taatgccggc gataccaata cggggagcag aaatcagggt catggtcggt ccatcagaac    2678
ggaaaaatca ggtgttggcg tcaagccggg catcgaaacg ggcacgggcc gcctcgattt    2738
cgggacggtt cgacagcgcc cactgaccga aagctt                             2774
```

<210> SEQ ID NO 6
<211> LENGTH: 262
<212> TYPE: PRT
<213> ORGANISM: Gluconobacter oxydans

<400> SEQUENCE: 6

```
Met Ser Lys Lys Phe Asn Gly Lys Val Cys Leu Val Thr Gly Ala Gly
1               5                   10                  15

Gly Asn Ile Gly Leu Ala Thr Ala Leu Arg Leu Ala Glu Glu Gly Thr
            20                  25                  30

Ala Ile Ala Leu Leu Asp Met Asn Arg Glu Ala Leu Glu Lys Ala Glu
        35                  40                  45

Ala Ser Val Arg Glu Lys Gly Val Glu Ala Arg Ser Tyr Val Cys Asp
    50                  55                  60

Val Thr Ser Glu Glu Ala Val Ile Gly Thr Val Asp Ser Val Val Arg
65                  70                  75                  80

Asp Phe Gly Lys Ile Asp Phe Leu Phe Asn Asn Ala Gly Tyr Gln Gly
                85                  90                  95

Ala Phe Ala Pro Val Gln Asp Tyr Pro Ser Asp Phe Ala Arg Val
            100                 105                 110
```

```
Leu Thr Ile Asn Val Thr Gly Ala Phe His Val Leu Lys Ala Val Ser
            115                 120                 125

Arg Gln Met Ile Thr Gln Asn Tyr Gly Arg Ile Val Asn Thr Ala Ser
        130                 135                 140

Met Ala Gly Val Lys Gly Pro Pro Asn Met Ala Ala Tyr Gly Ala Ser
145                 150                 155                 160

Lys Gly Ala Ile Ile Ala Leu Thr Glu Thr Ala Ala Leu Asp Leu Ala
                165                 170                 175

Pro Tyr Asn Ile Arg Val Asn Ala Ile Ser Pro Gly Tyr Met Gly Pro
            180                 185                 190

Gly Phe Met Trp Glu Arg Gln Val Glu Leu Gln Ala Lys Val Gly Ser
        195                 200                 205

Gln Tyr Phe Ser Thr Asp Pro Lys Val Val Ala Gln Gln Met Ile Gly
    210                 215                 220

Ser Val Pro Met Arg Arg Tyr Gly Asp Ile Asn Glu Ile Pro Gly Val
225                 230                 235                 240

Val Ala Phe Leu Leu Gly Asp Asp Ser Ser Phe Met Thr Gly Val Asn
                245                 250                 255

Leu Pro Ile Ala Gly Gly
            260

<210> SEQ ID NO 7
<211> LENGTH: 29
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (3)..(3)
<223> OTHER INFORMATION: n is a, g, t or c
<220> FEATURE:
<221> NAME/KEY: misc_feature
<222> LOCATION: (9)..(9)
<223> OTHER INFORMATION: n is a, g, t, or c
<220> FEATURE:
<221> NAME/KEY: misc_feature
<222> LOCATION: (15)..(15)
<223> OTHER INFORMATION: n is a, g, c, or t
<220> FEATURE:
<221> NAME/KEY: misc_feature
<222> LOCATION: (18)..(18)
<223> OTHER INFORMATION: n is a, g, c, or t
<220> FEATURE:
<221> NAME/KEY: misc_feature
<222> LOCATION: (21)..(21)
<223> OTHER INFORMATION: n is a, g, c, or t
<220> FEATURE:
<221> NAME/KEY: misc_feature
<222> LOCATION: (24)..(24)
<223> OTHER INFORMATION: n is a, g, c, or t
<220> FEATURE:
<221> NAME/KEY: misc_feature
<222> LOCATION: (27)..(27)
<223> OTHER INFORMATION: n is a, g, c or t

<400> SEQUENCE: 7
gcngayacna tgytngcngc ngtngtnmg                                    29

<210> SEQ ID NO 8
<211> LENGTH: 37
<212> TYPE: DNA
<213> ORGANISM: Artificial
<220> FEATURE:
<223> OTHER INFORMATION: synthetic DNA
<220> FEATURE:
<221> NAME/KEY: misc_feature
```

```
<222> LOCATION: (11)..(11)
<223> OTHER INFORMATION: n is a, g, c, or t
<220> FEATURE:
<221> NAME/KEY: misc_feature
<222> LOCATION: (14)..(14)
<223> OTHER INFORMATION: n is a, g, c, or t
<220> FEATURE:
<221> NAME/KEY: misc_feature
<222> LOCATION: (17)..(17)
<223> OTHER INFORMATION: n is a, g, c, or t
<220> FEATURE:
<221> NAME/KEY: misc_feature
<222> LOCATION: (20)..(20)
<223> OTHER INFORMATION: n is a, g, c, or t
<220> FEATURE:
<221> NAME/KEY: misc_feature
<222> LOCATION: (23)..(23)
<223> OTHER INFORMATION: n is a, g, c, or t
<220> FEATURE:
<221> NAME/KEY: misc_feature
<222> LOCATION: (32)..(32)
<223> OTHER INFORMATION: n is a, g, c, or t

<400> SEQUENCE: 8
cggaattcgc ngcngtngtn mgngarttyg gnaarcc                              37

<210> SEQ ID NO 9
<211> LENGTH: 35
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (15)..(15)
<223> OTHER INFORMATION: n is a, g, t or c
<220> FEATURE:
<221> NAME/KEY: misc_feature
<222> LOCATION: (21)..(21)
<223> OTHER INFORMATION: n is a, g, t or c
<220> FEATURE:
<221> NAME/KEY: misc_feature
<222> LOCATION: (27)..(27)
<223> OTHER INFORMATION: n is a, g, t or c
<220> FEATURE:
<221> NAME/KEY: misc_feature
<222> LOCATION: (30)..(30)
<223> OTHER INFORMATION: n is a, g, t or c
<220> FEATURE:
<221> NAME/KEY: misc_feature
<222> LOCATION: (33)..(33)
<223> OTHER INFORMATION: n is a, g, t or c

<400> SEQUENCE: 9
aaraarttya ayggnaargt ntgyytngtn acngc                                35

<210> SEQ ID NO 10
<211> LENGTH: 37
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (11)..(11)
<223> OTHER INFORMATION: n is a, g, c, or t
<220> FEATURE:
<221> NAME/KEY: misc_feature
<222> LOCATION: (14)..(14)
<223> OTHER INFORMATION: n is a, g, c, or t
<220> FEATURE:
<221> NAME/KEY: misc_feature
<222> LOCATION: (17)..(17)
<223> OTHER INFORMATION: n is a, g, c, or t
<220> FEATURE:
```

```
<221> NAME/KEY: misc_feature
<222> LOCATION: (20)..(20)
<223> OTHER INFORMATION: n is a, g, c, or t
<220> FEATURE:
<221> NAME/KEY: misc_feature
<222> LOCATION: (23)..(23)
<223> OTHER INFORMATION: n is a, g, c, or t
<220> FEATURE:
<221> NAME/KEY: misc_feature
<222> LOCATION: (32)..(32)
<223> OTHER INFORMATION: n is a, g, c, or t
<220> FEATURE:
<221> NAME/KEY: misc_feature
<222> LOCATION: (35)..(35)
<223> OTHER INFORMATION: n is a, g, c, or t

<400> SEQUENCE: 10
cggaattcgt nacnggnggn ggnaayathg gnytngc                        37

<210> SEQ ID NO 11
<211> LENGTH: 35
<212> TYPE: DNA
<213> ORGANISM: Artificial
<220> FEATURE:
<223> OTHER INFORMATION: synthetic DNA

<400> SEQUENCE: 11
cgttagaacg cgtaatacga ctcactatag ggaga                         35

<210> SEQ ID NO 12
<211> LENGTH: 31
<212> TYPE: DNA
<213> ORGANISM: Artificial
<220> FEATURE:
<223> OTHER INFORMATION: synthetic DNA

<400> SEQUENCE: 12
gatcttccga agtcccggac cacgctatcc g                             31

<210> SEQ ID NO 13
<211> LENGTH: 35
<212> TYPE: DNA
<213> ORGANISM: Artificial
<220> FEATURE:
<223> OTHER INFORMATION: synthetic DNA

<400> SEQUENCE: 13
gtacatattg tcgttagaac gcgtaatacg actca                         35

<210> SEQ ID NO 14
<211> LENGTH: 39
<212> TYPE: DNA
<213> ORGANISM: Artificial
<220> FEATURE:
<223> OTHER INFORMATION: synthetic DNA

<400> SEQUENCE: 14
cggaattccg tcacagacat aggagcgggc ttcgacgcc                     39

<210> SEQ ID NO 15
<211> LENGTH: 29
<212> TYPE: DNA
<213> ORGANISM: Artificial
<220> FEATURE:
<223> OTHER INFORMATION: synthetic DNA

<400> SEQUENCE: 15
ccgggattcc agagtttgag gcattcgga                                29
```

```
<210> SEQ ID NO 16
<211> LENGTH: 30
<212> TYPE: DNA
<213> ORGANISM: Artificial
<220> FEATURE:
<223> OTHER INFORMATION: synthetic DNA

<400> SEQUENCE: 16
ccgggatccg caagatggct cgcaggacgc                                           30
```